US00PP36202P2

(12) United States Plant Patent
Kleinwee

(10) Patent No.: US PP36,202 P2
(45) Date of Patent: Oct. 15, 2024

(54) ***PETUNIA* PLANT NAMED 'PEHY0085'**

(50) Latin Name: *Petunia hybrida*
Varietal Denomination: PEHY0085

(71) Applicant: SYNGENTA CROP PROTECTION AG, Basel (CH)

(72) Inventor: Theodorus Cornelis Maria Van Kleinwee, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/380,380

(22) Filed: Oct. 16, 2023

(51) Int. Cl.
*A01H 5/02* (2018.01)
*A01H 6/82* (2018.01)

(52) U.S. Cl.
USPC ..... Plt./356.21

(58) Field of Classification Search
USPC ..... Plt./356.21
CPC . A01H 5/02; A01H 5/00; A01H 6/824; A01H 6/82
See application file for complete search history.

(56) References Cited

U.S. PATENT DOCUMENTS

PP17,730 P2 * 5/2007 Sakazaki ..... A01H 6/824 Plt./356.21

OTHER PUBLICATIONS

Upov Pluto retrieved on Feb. 20, 2024 at https://pluto.upov.int/result, one page. (Year: 2024).*

* cited by examiner

*Primary Examiner* — June Hwu
(74) *Attorney, Agent, or Firm* — Dale Skalla

(57) ABSTRACT

A new *Petunia* plant named 'PEHY0085' particularly distinguished by its relatively small flowers, a pink flower color, relatively late flowering, trailing plant habit and very strong vigor.

1 Drawing Sheet

Latin name of the genus and species of the plant claimed: *Petunia hybrida.*

Varietal denomination: 'PEHY0085'.

BACKGROUND OF THE NEW PLANT

The present invention comprises a new *Petunia*, botanically known as *Petunia hybrida,* and hereinafter referred to by the variety name 'PEHY0085'.

'PEHY0085' is a product of a planned breeding program. The new cultivar has relatively small flowers, a pink flower color, relatively late flowering, a trailing plant habit and very strong vigor.

'PEHY0085' originated from a hybridization made in June 2017 in a controlled breeding environment in Enkhuizen, The Netherlands. The female parent was the proprietary selection 'P0296-296'. Compared to 'PEHY0085', it has a bigger flower, is earlier flowering and has less pronounced veins in the flower.

The male parent of 'PEHY0085' was the proprietary selection 'BB0504-2V'. Compared to 'PEHY0085', it has salmon flower color, is less vigorous and with a clear vein in the flower.

The resulting seeds were sown in September 2017. 'PEHY0085' was selected as one flowering plant within the progeny of the stated cross in November 2017 in a controlled environment in Enkhuizen, The Netherlands.

The first act of asexual reproduction of 'PEHY0085' was accomplished when vegetative stem cuttings were propagated from the initial selection in January 2018 in a controlled environment in Enkhuizen, The Netherlands.

BRIEF SUMMARY OF INVENTION

Horticultural examination of plants grown from cuttings of the plant initiated in January 2018 and continuing thereafter, has demonstrated that the combination of characteristics as herein disclosed for 'PEHY0085' are firmly fixed and are retained through successive generations of asexual reproduction.

'PEHY0085' has not been observed under all possible environmental conditions. The phenotype may vary significantly with variations in environment such as temperature, light intensity, and day length.

A Plant Breeder's Rights for this cultivar has been applied for in Canada on Nov. 29, 2023, No. 23-11543. 'PEHY0085' has not been made publicly available prior to the effective filing date of this application, notwithstanding any disclosure that may have been made less than one year prior to the effective filing date of this application by the inventor or another who obtained 'PEHY0085' directly from the inventor.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawings show typical flower and foliage characteristics of 'PEHY0085' with colors being as true as possible with an illustration of this type.

Figure 1:
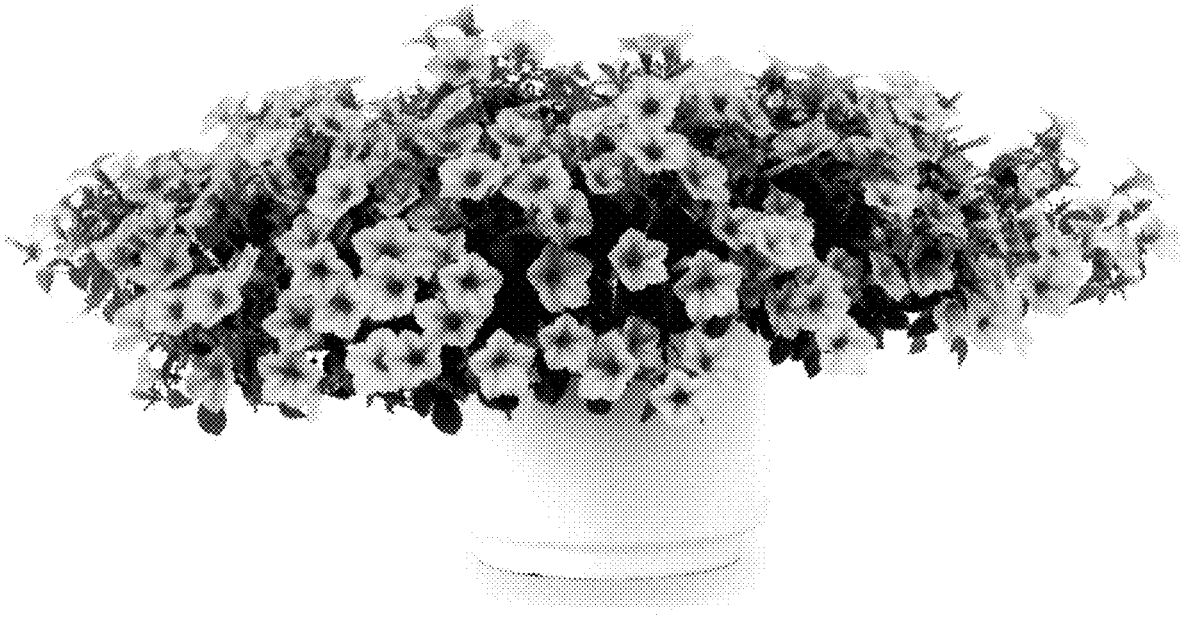
Figure 2:
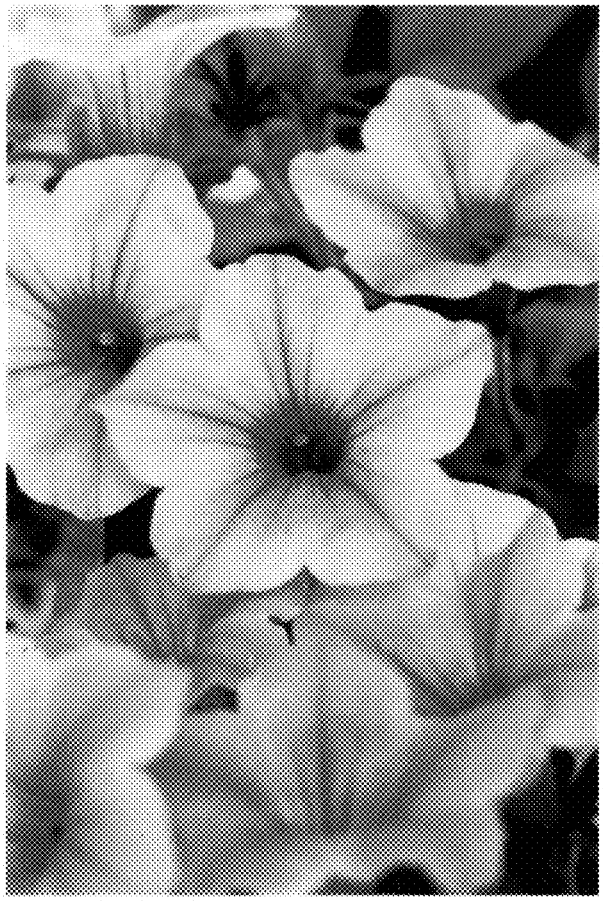

The photographic drawings show in FIG. 1 a flowering plant of the new variety and in FIG. 2 a close-up of the flowers.

DETAILED BOTANICAL DESCRIPTION

The aforementioned photographs were taken in May 2023 from plants growing indoors in 14 cm pots in Gilroy, California, USA. These plants were approximately 12 weeks of age.

The plant descriptions and measurements were taken in August 2023 in Andijk, The Netherlands on outdoor plants grown in containers. These plants were about 16 weeks old.

Color references are made to The Royal Horticultural Society Colour Chart (R.H.S.) 2001.

TABLE 1

DIFFERENCES BETWEEN THE NEW VARIETY 'PEHY0085' AND A SIMILAR VARIETY

| | 'PEHY0085' | 'USTUNI6001' (U.S. Plant Pat. No. 17,730) |
|---|---|---|
| Earliness: | Medium to late flowering | Medium early |
| Flower size: | Small | Medium |
| Pollen color: | RHS 101C | RHS 198B |

Plant:

*Form, growth and habit.*—Trailing plant habit.
*Plant height.*—17 cm.
*Plant height (inflorescence included).*—19 cm.
*Plant diameter (width).*—Approximately 80 cm.

Roots:

*Number of days to initiate and produce roots.*—14 days at about 22° C.
*Type.*—Fine, fibrous, free branching.
*Color.*—RHS 158D.

Foliage:

*Arrangement.*—Alternate, simple; sometimes opposite, decussate.
*Immature leaf, color upper surface.*—RHS 138A.
*Immature leaf, color lower surface.*—RHS 138C.
*Mature leaf, color upper surface.*—RHS 137B.
*Mature leaf, color lower surface.*—RHS 138B.
*Length.*—2.6-3.4 cm.
*Width.*—1.1-1.8 cm.
*Shape.*—Ovate.
*Base shape.*—Acuminate.
*Apex shape.*—Acute.
*Margin.*—Entire.
*Texture, upper surface.*—Densely covered with short hairs.
*Lower surface.*—Densely covered with short hairs.
*Color of veins, upper surface.*—RHS 144A.
*Color of veins, lower surface.*—RHS 144A.
*Petiole color.*—RHS 144A.
*Length.*—0.3 cm.
*Diameter.*—0.2 cm.
*Petiole texture.*—Densely covered with short hairs.

Stem:

*Quantity of main branches per plant.*—5-6.
*Color of stem.*—RHS 144A.
*Length of stem.*—34 cm.
*Diameter.*—0.4 cm.
*Length of internodes.*—3.0-4.0 cm.
*Texture.*—Dense, mostly glandular short hairs.
*Color of pedicel.*—RHS 144A.
*Length of pedicel.*—1.8-2.1 cm.
*Diameter of pedicel.*—0.2 cm.
*Texture of pedicel.*—Densely covered with short hairs.

Inflorescence:

*Type.*—Flowers solitary in upper leaf axis.
*Floret type.*—Funnel-shaped; 5 lobed petals; fused at base.
*Blooming habit.*—Relatively late flowering in greenhouse, flowering throughout the summer months.
*Quantity of inflorescences per plant.*—Approximately 380.
*Lastingness of individual blooms on the plant.*—About 7 days.
*Fragrance.*—Medium smell.

Bud (just when opening):

*Color.*—RHS 73D with spots of RHS 73B at top, RHS 61B with veins RHS 187A towards base.
*Length.*—2.7 cm.
*Width.*—0.6 cm.
*Shape.*—Oblong.

Immature inflorescence:

*Flower horizontal diameter.*—2.5 cm.
*Color petals, upper surface.*—RHS 68A.
*Color petals, lower surface.*—RHS 73C, RHS 68B around veins.
*Color of veins, upper and lower surface.*—RHS 67A.

Mature flower:

*Flower horizontal diameter.*—4.0 cm.
*Flower height (vertical).*—3.0 cm.
*Color upper surface.*—RHS 68B with veins RHS 67A.
*Color lower surface.*—RHS 68D, RHS 67A around veins.
*Conspicuousness of veins.*—Medium.
*Apex shape.*—Acuminate.
*Margin.*—Entire.
*Waviness of margin.*—Medium.
*Petal lobation.*—Medium to strong.
*Petal texture, upper surface.*—Smooth.
*Petal texture, lower surface.*—Smooth, occasionally a short hair mainly along veins.
*Corolla tube color outside.*—RHS 67B with veins RHS 153C.
*Corolla tube color inside.*—RHS 68C with veins RHS 74A.
*Conspicuousness of veins in tube.*—Medium.
*Corolla tube length.*—1.5 cm.
*Corolla tube texture, outside.*—Dense and short glandular hairs.
*Corolla tube texture, inside.*—Glabrous.

Calyx:

*Color of sepal, upper surface.*—RHS 137B.
*Color of sepal, lower surface.*—RHS 138C.
*Length.*—0.8 cm.
*Width.*—0.1 cm.
*Shape.*—Ensiform.
*Apex shape.*—Acute.
*Base.*—Fused.
*Margins.*—Entire.
*Texture, upper surface.*—Densely covered with short glandular hairs.
*Lower surface.*—Densely covered with short glandular hairs.

Reproductive organs:

*Pistil.*—1.

*Length*.—1.4 cm.
*Style color*.—RHS 149B, RHS 72A near Stigma.
*Style length*.—1.4 cm.
*Stigma color*.—RHS 91D, RHS 88B at margin.
*Stamens*.—Quantity per flower: 5.
*Color of filaments*.—RHS 145D.
*Length filaments*.—1.4 cm.
*Anther color*.—RHS 97A.
*Anther length*.—0.2 cm.
*Anther shape*.—Elliptical.
*Color of pollen*.—RHS 101C.
*Pollen amount*.—Abundant.
*Fertility/seed set*.—Has not been observed on this hybrid.
*Disease/pest resistance*.—Has not been observed on this hybrid.

What is claimed is:

1. A new and distinct variety of *Petunia* plant named 'PEHY0085' substantially as illustrated and described herein.

* * * * *